US006697667B1

(12) United States Patent
Lee et al.

(10) Patent No.: US 6,697,667 B1
(45) Date of Patent: Feb. 24, 2004

(54) APPARATUS AND METHOD FOR LOCATING CORONARY SINUS

(75) Inventors: Jeong S. Lee, Diamond Bar, CA (US); Bruce Wilson, Temecula, CA (US); Deborah Kilpatrick, Mountain View, CA (US); Robert Ainsworth, Scotts Valley, CA (US); Bridget A. Hurley, Mountain View, CA (US); Jeffrey T. Ellis, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 121 days.

(21) Appl. No.: 09/872,248

(22) Filed: May 31, 2001

(51) Int. Cl.[7] .............................. A61B 5/02; G01N 15/02
(52) U.S. Cl. ...................... 600/479; 600/585; 604/523; 356/336; 385/119
(58) Field of Search ................................ 600/342, 373, 600/374, 407, 424, 437, 439, 454, 478, 479, 504, 508, 585, 115, 116, 117; 604/506, 507, 523, 525, 526, 528; 606/108; 607/122; 356/335, 336, 477; 385/115, 116, 117, 118

(56) References Cited

U.S. PATENT DOCUMENTS

| | | | |
|---|---|---|---|
| 4,538,618 A | * | 9/1985 | Rosenberg et al. ......... 600/407 |
| 4,587,972 A | | 5/1986 | Morantte, Jr. |
| 4,671,288 A | | 6/1987 | Gough |
| 4,794,931 A | | 1/1989 | Yock |
| 4,887,605 A | | 12/1989 | Angelsen et al. |
| 4,920,967 A | | 5/1990 | Cottonaro et al. |
| 4,926,875 A | | 5/1990 | Rabinovitz et al. |
| 5,022,399 A | | 6/1991 | Biegeleisen |
| 5,047,213 A | | 9/1991 | Finlan et al. |
| 5,167,233 A | | 12/1992 | Eberle et al. |
| 5,284,146 A | | 2/1994 | Czar et al. |
| 5,325,860 A | | 7/1994 | Seward et al. |

(List continued on next page.)

FOREIGN PATENT DOCUMENTS

JP      1-308548 A    * 12/1989    ................ 600/342

OTHER PUBLICATIONS

Beekhuizen H, van Furth R. "Monocyte Adherence to Human Vascular Endothelium." *Journal of Leukocyte Biology* 1993, vol. 54, 363–378.

Casscells W, Hathorn B, David M, Krabach T, Vaugh W, McAllister H, et al., "Thermal detection of Cellular Infiltrates in Living Atherosclerotic Plaques: Possible Implications for Plaque Rupture and Thrombosis." *Lancet* 1996, vol. 347, 1447–1451.

Einav S. "Laser Doppler Fiberscope Anemometer for In Vivo Blood Flow Measurements." *Optical Fibers in Medicine VIII* 1993, 62–73.

Hangiandreou N, Toggart E, Mistretta C. "Investigation of the Performance of Two Types of the Doppler Catheter in Vitro." *Catherization and Cardiovascular Diagnosis* 1989, vol. 18, 108–117.

(List continued on next page.)

*Primary Examiner*—Willis R. Wolfe
(74) *Attorney, Agent, or Firm*—Blakely, Sokoloff, Taylor & Zafman LLP (57) ABSTRACT

An intravascular device for locating a coronary sinus of a patient's heart and method of using the same. In one embodiment, the intravascular device includes an elongated member having at least one lumen and at least one optical fiber coupled to the elongated member. The optical fiber has a distal end configured to contact with a blood flow within the patient's heart and a proximal end coupled to a laser Doppler velocimetry system for performing a plurality of laser Doppler velocity measurements of the blood flow within the heart to locate the coronary sinus of the heart. Incorporating LDV technology into an intravascular device such as a catheter or a guidewire system provides diagnostic information of the physiologic environment of the lesion before, during, or after a therapeutic procedure.

27 Claims, 7 Drawing Sheets

U.S. PATENT DOCUMENTS

| | | | |
|---|---|---|---|
| RE34,695 E | | 8/1994 | Mar et al. |
| 5,345,940 A | | 9/1994 | Seward et al. |
| 5,571,086 A | | 11/1996 | Kaplan et al. |
| 5,582,171 A | | 12/1996 | Chornenky et al. |
| 5,603,820 A | | 2/1997 | Malinski et al. |
| 5,722,963 A | * | 3/1998 | Lurie et al. ................. 604/525 |
| 5,744,902 A | | 4/1998 | Vig |
| 5,752,518 A | * | 5/1998 | McGee et al. .............. 600/424 |
| 5,756,351 A | | 5/1998 | Isacoff et al. |
| 5,782,760 A | | 7/1998 | Schaer |
| 5,855,563 A | | 1/1999 | Kaplan et al. |
| 5,873,835 A | | 2/1999 | Hastings et al. |
| 5,876,345 A | | 3/1999 | Eaton et al. |
| 5,902,308 A | | 5/1999 | Murphy |
| 5,904,651 A | * | 5/1999 | Swanson et al. ............ 600/407 |
| 5,919,129 A | | 7/1999 | Vandre |
| 5,935,075 A | | 8/1999 | Casscells et al. |
| 5,951,471 A | | 9/1999 | de la Rama et al. |
| 5,951,482 A | | 9/1999 | Winston et al. |
| 5,957,903 A | | 9/1999 | Mirzaee et al. |
| 5,980,471 A | | 11/1999 | Jafari |
| 5,984,909 A | | 11/1999 | Lurie et al. |
| 6,001,085 A | | 12/1999 | Lurie et al. |
| 6,023,638 A | | 2/2000 | Swanson |
| 6,141,576 A | | 10/2000 | Littmann et al. |
| 6,166,806 A | * | 12/2000 | Tjin ........................... 356/336 |
| 6,277,107 B1 | * | 8/2001 | Lurie et al. ................. 604/528 |
| 6,522,913 B2 | * | 2/2003 | Swanson et al. ............ 600/478 |
| 2002/0029030 A1 | * | 3/2002 | Lurie et al. ................. 604/506 |

OTHER PUBLICATIONS

Ikeda U, Takahashi M, Shimada K. "Monocyte–Endothelial Cell Interaction in Atherogenesis and Thrombosis." *Clinical Cardiology* 1997, vol. 21, 11–14.

Kern M, de Bruyne B, Pijls N. "From Research to Clinical Practice: Current Role of Intracoronary Physiologically Based Decision making in the Cardiac Catherterization Laboratory." *Journal of the American College of Cardiology* 1997, vol. 30, 613–620.

Kilpatrick D, Kajiy A F, Ogasawara Y. "Fiber Optic Lase Doppler Measurement of Intravascular Velocity." *Australasian Physical and Engineering Sciences in Medicine* 1998, vol. 11, 5–14.

Nishhara H, Koyama J, Hoki N, Kajiya F, Hironaga M, Kano M. "optical–Fiber Laser Doppler Velocimeter for High–Resolution Measurement of Pulsatile Blood Flows." *Applied Optics* 1982, vol. 21, 1785–1790.

Serruys P, di Mario C, Piek J, Shcroeder E, Vrints C, Probst P, de Bruyne B, et al., "Prognostic Value of Intracoronary Flow Velocity and Diameter Stenosis in Assessing the Short–and Long–Term Outcomes of Coronary Balloon Angioplasty: *The Debate Study*." Circulation 1997, vol. 96, 3369–3377.

Stefandadis C, Diamantopoulos L, Vlachopoulos C, Tsiamis E, Dernellis J, Toutouzas K, et al., "Thermal Heterogeneity Within Human Atherosclerotic Coronay Arteries Detected In Vive: A New Method of Detection by Application of a Special Thermography Catheter." *Circulation* 1999, vol. 99, 1965–71.

Doucette J., Corl D., Payne H., Flynn A., Goto M., Nassi M., Segal J. "Validation of a Doppler Guidewire for Intravascular Measurement of Coronary Artery Flow Velocity", Circulation 1992, vol. 85, 382–385.

Dib N., Bajwa T., Shalev Y., Nesto R. Schmidt D., "Validation of Doppler FloWire for Measurement of Coronary Flow Reserve in Humans". *Catheterization and Cardiovascular Diagnosis* 1998, vol. 45, 382–385.

Pijls N., Van Gelder B., Van der Voort P., Peels K., Bracke F., Bonnier H., El Gamal M., "Fractional Flow Reserve: A Useful Index to Evaluate the influence of an Epicardial Coronary Stenosis on Myocardial Blood Flow." *Circulation* 1995, vol. 92, 3183–3193.

Bridget Hurley's Lab Book 5449, pp. 28–29.

Jeff Ellis Lab Book 5528, pp. 103–107.

Davis R., "Bursting The Deadly Danger Of Aortic Aneurysms", USA Today, Mar. 16, 2000, Section 10D.

Krohn D., "Two Ways of Sensing with Fibers for Two Kinds of Applications", 1998 *The Photonics Design and Applications Handbook*, Sensors, H–203.

Engineering & Marketing Staff, "An Introduction to Fiber Optics", *1998 The Photonics Design and Applications Handbook*, Fiber Optics, H–176.

Bhatia V., Murphy K., de Vires M., Sen M., D'Alberto T., "A Comparative Evaluation of the Types and Applications of Various Sensors" 1998, *The Photonics Design and Applications Handbook*, Sensors, H–199.

McCann B., "Three Silica–Core Fibers Rise to Top in Medical Laser Uses", 1998, *The Photonics Design and Applications Handbook*, Fibers/Medical Lasers, H–209.

McCam B., "Fiber Holds the Key to Medical Lasers' Success", May 1990, *Photonics Spectra*, p. 127.

Moslem A., "Transmission properties of optical fibers at two laser wavelengths; 660 nm & 2100 nm", PTICAL Materials, Aug. 19, 1991, Center for Laser Research, Oklahoma State University, p. 27–41.

* cited by examiner

APPARATUS AND METHOD FOR LOCATING CORONARY SINUS

FIELD OF THE INVENTION

This invention relates to the field of intravascular medical diagnosis and treatment. More specifically, the present invention relates to an intravascular device for locating the ostium of the coronary sinus in the right atrium of the heart.

DESCRIPTION OF RELATED ART

Atherosclerosis is a common human ailment arising from the deposition of fatty-like substances, referred to as atheroma or plaque, on the walls of systemic, peripheral, and coronary blood vessels. These plaques restrict the flow of blood through the affected vessels. Of particular concern is when these plaques develop within the blood vessels that feed the muscles of the heart. In healthy hearts, cardiac blood perfusion results from the two coronary arterial vessels, the left and right coronary arteries which perfuse the myocardium from the epicardial surface inward towards the endocardium. The blood flows through the capillary system into the coronary veins and into the right atrium via the coronary sinus. When atherosclerosis occurs within the arteries of the heart it leads to myocardial infarctions, or heart attacks, and ischemia due to reduced blood flow to the heart muscle.

Increasingly, procedures have been designed to investigate, analyze and diagnose the cause of arrhythmias that occur in the heart. Methods to diagnose the cause of certain arrhythmias include connection of a patient to patch leads placed on the chest of the patient to record the electrical activity of the heart. These procedures are commonly called electrocardiograms. However, more specific information with regard to the patient's arrhythmia can be gained by placing sensing electrodes at specific locations in the heart. Once these electrodes are in a predetermined, precise location within the heart, readings can be taken which will help determine the types of arrhythmias and diagnose the problems of the patient's heart.

These electrophysiological analyses require the precise placement of the sensing electrodes within the heart. Examples of locations for the placement of these electrodes include designated points within the right atrium, the right ventricle, near the Bundle of His and in the coronary sinus. The coronary sinus is the largest cardiac vein which serves as a venous conduit from smaller veins within the myocardium to the right atrium. The coronary sinus extends from an opening, called ostium, for the coronary sinus in the right atrium, along the posterior of the heart to the left side of the heart along the atrioventricular border.

Catheters have been in use in medical procedures for many years. Recently, catheters have become more commonly used within the heart and vascular system. For example, catheters can be used to reduce or remove vascular deposits, for example used in balloon angioplasty and stent deployment procedures. Treating congestive heart failure (CHF) interventionally is generally performed using multiple devices, such as guiding catheters, guidewires, sheaths, pacemakers and pacing leads, with the goal being the placement of the pacing lead deep into the coronary sinus.

One of the difficulties in performing procedures within the coronary sinus is finding the ostium to the coronary sinus while the heart is beating. There are a number of anatomical structures within the right atrium which can be easily confused with the coronary sinus. Further, these particular features of the heart do not show up well on a fluoroscope, thus making the procedure quite difficult and time consuming for the physician. One of the difficulties in performing procedures within the heart is finding the ostium of the coronary sinus while the heart is beating. Adding to the difficulty is CHF patients generally have enlarged hearts, which tend to change the location of the ostium from that of a normal heart. Using fluoroscopic techniques also do not work well because blood flow out of the vein pushes the contrast media away from the ostium. Current devices used for locating the coronary sinus generally include guiding catheters, electrophysiological catheters and ultrasonic catheters. Electrophysiological catheters are designed to detect electrical activity or signals within a patient's heart, while ultrasonic catheters incorporate ultrasonic transducer technology to send and receive acoustic signals that are then processed into images. These devices have a number of drawbacks. One major problem is the unstable positioning of electrophysiological catheters inside the right atrium of the heart. When a catheter is not stabilized, the heart's electrical conduction pattern is difficult to establish and map the coronary sinus. Another significant disadvantage of existing electrophysiological catheters to locate the coronary sinus is that the medical techniques employing these catheters are complicated and time consuming, requiring repeated manipulation and movement of the catheter.

Ultrasonic catheters have disadvantages and limitations similar to those of electrophysiological catheters, including susceptibility to signal loss, extensive operator input, etc. Another limitation of current ultrasonic catheters is that because the ultrasonic crystals are mounted on either the side or end of the catheter body, instability of the catheter tip position can result, making it difficult to localize the particular site.

The disadvantages of current generation electrophysiological and ultrasonic catheters can be overcome by integrating laser Doppler velocimetry (LDV) technology within an intravascular device such as a catheter or a guidewire. Laser Doppler velocimetry is a technique for measuring the speed of small particles. Generally, for LDV measurements, small particles suspended in a fluid are illuminated by a laser beam and the light scattered to various angles is compared to light in a reference beam to determine the Doppler shift of the scattered light. The Doppler shift of the light depends on the speed of the particles and the angle of measurement.

SUMMARY OF THE INVENTION

An intravascular device for locating a coronary sinus of a patient's heart and method of using the same are described. In one embodiment, the intravascular device includes an elongated member having at least one lumen and at least one optical fiber coupled to the elongated member. The optical fiber has a distal end configured to contact with a blood flow within the patient's heart and a proximal end coupled to a laser Doppler velocimetry system for performing a plurality of laser Doppler velocity measurements of the blood flow within the heart to locate the coronary sinus of the heart. Incorporating LDV technology into an intravascular device such as a catheter or a guidewire system provides diagnostic information of the physiologic environment of the lesion before, during, or after a therapeutic procedure.

BRIEF DESCRIPTION OF THE DRAWINGS

The present invention is illustrated by way of example and not limitation in the accompanying figures.

DETAILED DESCRIPTION OF THE INVENTION

Embodiments of apparatuses and methods for locating the coronary sinus of a patient's heart are described. In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

Figure 1A:
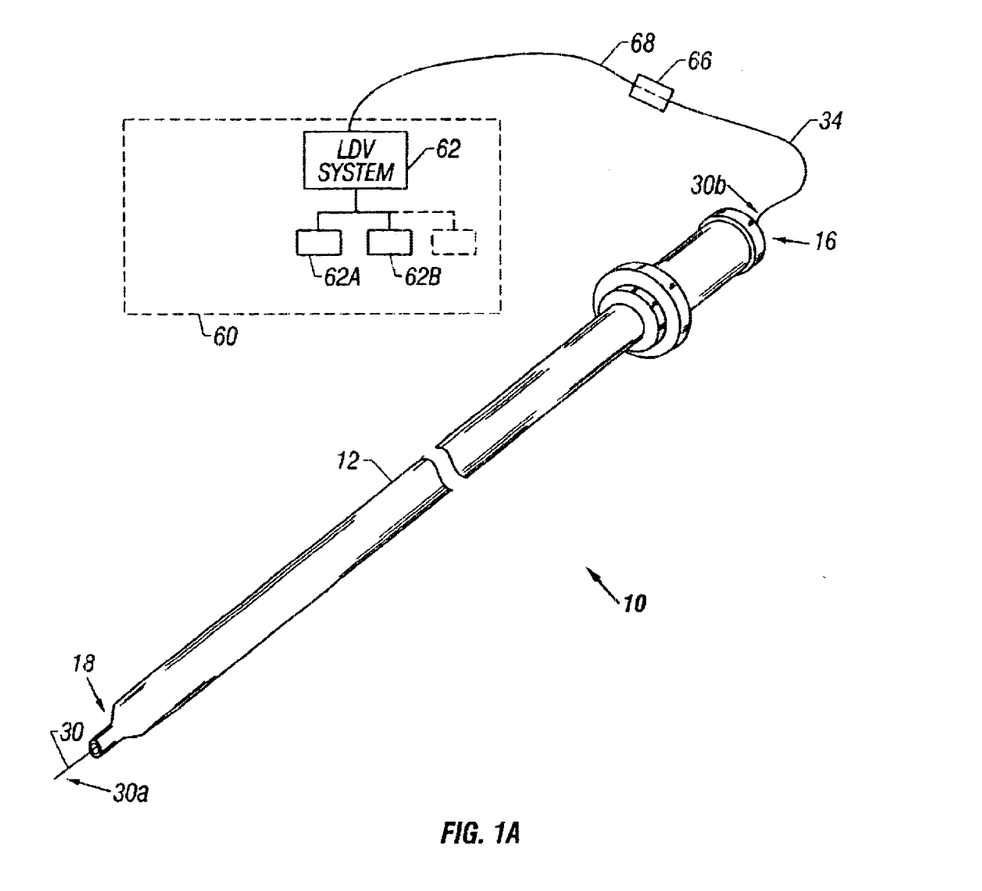
FIG. 1A is a perspective view illustrating generally an embodiment of an intravascular device for locating the coronary sinus of a patient's heart coupled to an LDV apparatus/data measurement system.
Figures 1B, 1C:
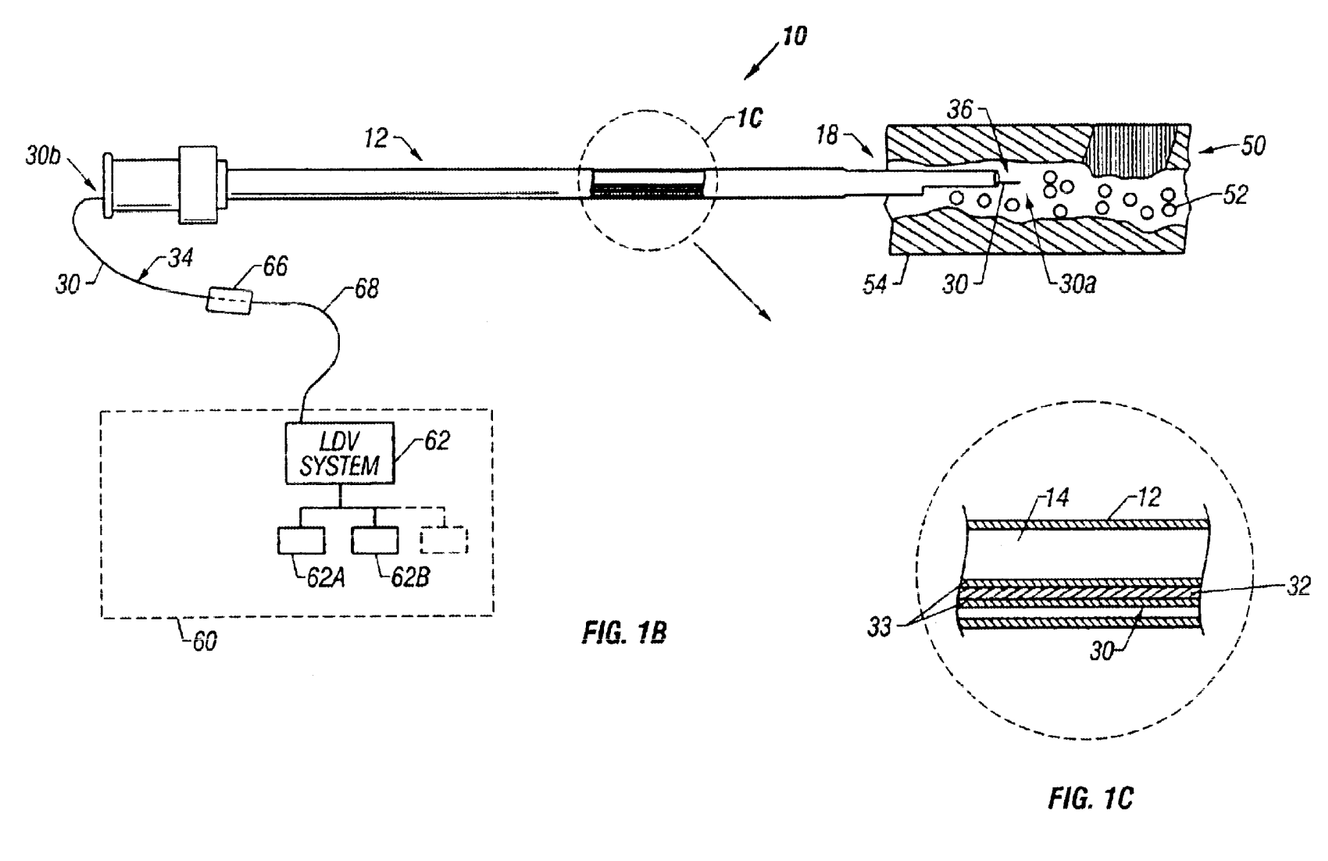
FIG. 1B is a schematic view of intravascular device of FIG. 1A positioned within a vasculature of a patient.
FIG. 1C is a schematic partial section side view of the elongated member of intravascular device of FIG. 1B showing the optical fiber positioned therethrough.

FIGS. 1A–1C illustrate generally an embodiment of an intravascular device 10 for locating the coronary sinus of a patient's heart coupled to an LDV system 60. FIG. 1A is a perspective view of intravascular device 10. In FIG. 1B, the intravascular device 10 is schematically shown to be inserted into a body lumen, e.g. vasculature 50 of a patient. The intravascular device 10 may include any medical device, such as a guiding catheter, a treatment catheter, or a therapeutic guidewire, used to treat intravascular conditions.

The intravascular device 10 generally includes an elongated member 12 having proximal and distal sections 16, 18, and at least one lumen 14 (shown in partial section side view of FIG. 1C) extending through at least a portion of the elongated member. The intravascular device 10 further includes at least one optical fiber 30 that may extend through the lumen 14 or is positioned along the outside surface of the elongated member 12. The optical fiber 30 has a distal end 30a configured to contact with a blood flow within the patient's heart and a proximal end 30b configured to be coupled to a laser Doppler velocimetry (LDV) system 60 for performing a plurality of laser Doppler velocity measurements of the blood flow within the heart to locate the coronary sinus of the heart. It will be noted that it is within the scope of the present invention to have the intravascular device 10 incorporate multiple optical fibers or a fiber optic bundle for the optical fiber 30.

Generally, optical fiber 30 may include a thin filament of drawn or extruded glass or plastic/polymer having a central core 32 and a cladding 33 of lower index material to promote internal reflection of light (as shown in the side view partial section enlargement of FIG. 1C). The central core 32 is the light-transmitting portion of the optical fiber 30.

Continuing with reference to FIGS. 1A–1C, in an embodiment, optical fiber 30 is a single strand, single-mode glass optical fiber generally disposed within lumen 14 of the elongated member 12. Optical fiber 30 may be fixedly coupled to one or more points within the elongated member 12 or alternatively, it may be movable, e.g. slideable, within the elongated member lumen 14. Optical fiber 30 typically extends slightly beyond both the proximal and distal ends 16, 18 of elongated member 12. A proximal extension length 34 of optical fiber 30 allows for connection of optical fiber 30 to an LDV system 62 through a mechanical coupler 66 and an LDV optical fiber 68. A distal extension length of optical fiber 30 allows for any necessary steps required to make the optical fiber tip 36 flush with, or extend slightly beyond the distal end 18 of the elongated member 12. Such steps can include, but are not limited to, cleaving the optical fiber 30 at an angle, cutting the fiber 30 with a perpendicular face, or removing the fiber cladding as necessary to optimize light transmission/reception.

Optical fiber 30 may be manufactured of glass or plastic and may have an outer diameter of about 100–250 micrometers ($\mu$m) (0.004–0.01 inches). As an example, optical fiber 30 may have an outer diameter of about 155 $\mu$m (0.006 inches) with a core 32 diameter of about 9.3 $\mu$m (0.000372 inches). The LDV optical fiber 68 may also be manufactured of glass or plastic and may have an outer diameter of about 200–350 $\mu$m (0.008–0.014 inches). In an example embodiment, LDV optical fiber 68 may have an outer diameter of about 250 $\mu$m (0.01 inches) with a core diameter of about 9.3 $\mu$m (0.000372 inches). It will be noted that selection of optical fibers 30, 68 is not limited to only the example embodiments and diameters discussed above. Other more flexible optical fibers, such as those with polymer-based claddings, as well as optical fibers having smaller diameters may be used in practicing this invention.

During its use in a medical procedure, the fiber optic 30 of intravascular device 10 transmits and receives light for determining fluid flow velocities through a laser Doppler velocimetry (LDV) technique. Laser Doppler velocimetry is a non-intrusive method for measuring flow velocities. The LDV method is a light-based technique that focuses a small sample volume, often on the order of $10^{-4}$ mm$^3$, very near the tip of the medical device 10 for detailed interrogation of a flow space near the tip or within the intravascular device 10. Generally, to perform LDV measurements, light is transmitted from a laser source 62A in the LDV system 62 through the optical fibers 30, 34, 68 and is scattered off of formed blood elements 52. The scattered light is collected by a detector 62B in the LDV system 62 as the light travels back through the optical fibers 30, 34, 68. The frequency content of the scattered light is indicative of the fluid velocity at the measurement site.

In an alternative embodiment, the LDV technology 62 uses intersecting two or more beams from a light source 62A, for example a laser source, and advanced optical data collection and processing equipment 62B to measure motion of individual minute particles as they pass through an imposed fringe pattern. The crossing of laser beams creates a "measurement volume" which consists of an interference fringe pattern of planar layers of high and low intensity light. Minute particles (e.g., 1 μm to 10 μm) present in the fluid backscatter the laser light with a frequency proportional to the flow velocity when passing through the measurement volume. The backscattered light is typically converted to an electrical signal with a photodetector or similar device. By using Fast Fourier Transform (FFT) techniques, the Doppler frequency is determined. The flow velocity is calculated with the known distance between the interference fringes and the measured frequency.

Figures 2, 3A, 3B, 3C:
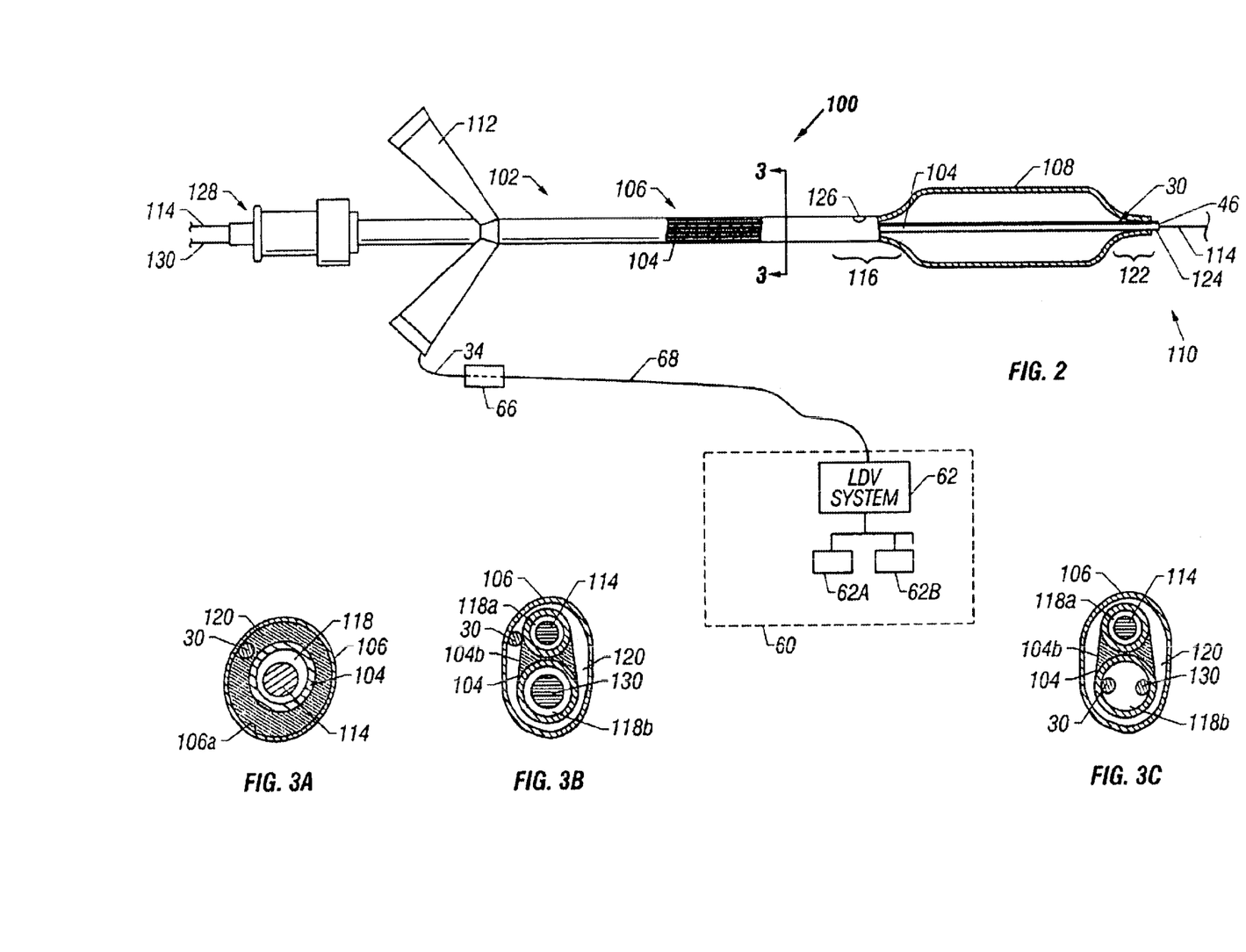
FIG. 2 is a side view partial section of an embodiment of a catheter for locating the coronary sinus of a patient's heart coupled to an LDV apparatus/data measurement system.
FIG. 3A is a cross-sectional view of the catheter of FIG. 2 having a single lumen inner member and having an optical fiber positioned within an intraluminal space of the catheter shaft outer member.
FIG. 3B is a cross-sectional view of an alternate embodiment of catheter of FIG. 2 having a multi-lumen inner member and an optical fiber positioned within an intraluminal space of the catheter shaft outer member.
FIG. 3C is a cross-sectional view of another embodiment of catheter of FIG. 2 having a multi-lumen inner member and an optical fiber positioned within a lumen of the catheter shaft inner member.

Catheter for Performing LDV Blood Flow Measurements to Locate Coronary Sinus FIGS. 2 and 3A–3C schematically illustrate an embodiment of a catheter 100 representing features of this invention. Catheter 100 is an over-the wire (OTW) type catheter configured to perform a therapeutic treatment and includes an optical fiber 30 for performing LDV blood flow measurements. FIG. 2 is a schematic side view representation of the OTW catheter 100. FIG. 3A illustrates a cross-sectional area of the OTW catheter 100 of FIG. 2 having an inner member with a single lumen configuration and an optical fiber disposed within an intraluminal gap formed between the inner and outer members. FIG. 3B illustrates a cross-sectional area of another embodiment of OTW catheter 100 of FIG. 2 having an inner member with a multilumen configuration and an optical fiber disposed within an intraluminal gap formed between the inner and outer members. FIG. 3C illustrates a cross-sectional area of an alternative embodiment of OTW catheter 100 of FIG. 2 having an inner member with a multi-lumen configuration and an optical fiber disposed within a lumen of the inner member.

When disposed within catheter 100, optical fiber 30 may be positioned in a number of configurations, for example within an intraluminal gap or lumen between the catheter shaft inner and outer members, or within a lumen of the shaft inner member. Optical fiber 30 may be fixedly coupled to the balloon catheter 100 at a least one point thereof. Alternatively, optical fiber 30 may be movable, i.e., slideable within the balloon catheter 100. These fiber optic/catheter configurations are discussed in detail below.

Continuing with reference to FIGS. 2 and 3A–3C, in an embodiment, catheter 100 includes an elongated catheter shaft 102 having an inner tubular member 104 and an outer member 106 disposed about the inner tubular member 104. An expandable member 108, for example an inflatable balloon 108, may be coupled to a distal end 110 of the elongated catheter shaft 102. An adapter 112, such as a proximal triple port sidearm 112, is secured to the proximal ends of the inner and outer members 104, 106. Triple port sidearm 112 allows a port for guidewire 114 insertion, another port for passage of an inflating medium (not shown) for balloon 108 inflation, and a third port for insertion of the optical fiber 30 for performing LDV blood flow measurements.

The catheter shaft tubular inner member 104 generally extends from the proximal sidearm 112 to a catheter distal tip 110 while the outer member 106 extends from the proximal sidearm 112 to a balloon proximal seal area 116, where the outer member 106 is placed over and is fused to the proximal end of the balloon 108. Tubular inner member 104 may include at least one lumen 118, 118a–b longitudinally disposed therethrough that may be used by a guidewire 114 to position the catheter's distal tip 110, including the balloon 108, over a predetermined location within the body lumen that is to be treated. For a catheter configuration with an inner member 104 having multiple lumens 118a, 118b (as shown in FIG. 3B), one lumen 118a is used as a guidewire lumen for guidewire 114 while the other lumen 118b may be used as a treatment lumen, for example as a radiation source lumen for passage of a radiation source 130 to a treatment site within a body lumen.

Balloon 108 may have a single lumen/single lobe configuration, a multilumen/multi-lobe configuration, or a combination thereof and may include tapered proximal and distal ends for enhanced treatment delivery, improved body lumen access, better balloon refolding, etc. The configuration of the inflatable balloon 108 generally depends on the type of application in which the balloon catheter 100 is to be used as well as other factors such as manufacturing preferences. For example, when used in the dilatation of a vessel, inflatable balloon 108 may generally have a single lumen/single lobe design. When used for radiation therapy or drug delivery applications, catheter 100 may typically include a balloon 108 having a multi-lumen/multi-lobe configuration for better centering or positioning within a body lumen.

Continuing with reference to FIGS. 2 and 3A–3C, in one embodiment, optical fiber 30 is inserted into the intraluminal space or gap 120 between the outer member 106 and the inner member 104. In one configuration, optical fiber 30 may be movable, e.g. slideable, within intraluminal space or gap 120. In another configuration (shown in FIG. 3A), optical fiber 30 may be fixedly coupled (i.e., secured) to the inner surface 106a of the shaft outer member 106 at one or more points along the outer member 106. This configuration will allow fiber 30 to bend and "flex" easily as the catheter 100 tracks through tortuous anatomy. For optical transmission, the distal tip of fiber 30 may be exposed to the vasculature of a patient through a notch 126 or an optical window present in the outer member 106 or it may be slightly extending past the distal tip 110 of catheter 100.

In another embodiment (as shown in exemplary embodiment of FIG. 3B), fiber 30 could be secured to the outer surface 104b of the shaft inner member 104 (configured to receive a guidewire 114 and radiation source 130) that extends to a distal tip 110 of the catheter 100. In this configuration, optical fiber 30 could be bonded to the inner member 104 at the distal balloon seal 122. This configuration would allow the tip of optical fiber 30 to be exposed for optical transmission at the distal tip 110 of catheter 100.

In an alternative embodiment (as shown in exemplary embodiment of FIG. 3C), at least one optical fiber 30 could be positioned within lumen 118b of the shaft inner member 104, while lumen 118a would be configured to receive a guidewire 114 and/or an inflation medium therethrough. In this configuration, optical fiber 30 could be bonded to the inner member 104 or may be movable, e.g. slideable within lumen 118b.

The catheter shaft outer member 106 may be formed of suitable polymeric material such as high-density polyethylene (HDPE), a polyester such as Hytrel® (trademark of DuPont), poly-ether-ether-ketone (PEEK) or a variety other polymeric materials. The balloon 108 may be manufactured using balloon materials, such as Pebax™, nylon, polyethylene, polyurethane, or polyester. Materials for use in fabricating the balloon 108 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.). The catheter shaft inner tubular member 104 may be formed of the same material as the outer member 106 or a lubricious material such as a fluoropolymer or a hydrophilic material, e.g. the ethylene ethyl acrylate co-polymer. The low friction surface of the inner wall of tubular inner member 104 facilitates the advancement of a guidewire 114 within the inner member lumen 118. The tubular inner member 104 may be a co-extruded member so that the exterior is compatible for fusion bonding to the balloon 108 and the interior has a lubricious surface. In an embodiment, catheter shaft tubular inner member 104 is manufactured as a co-extruded member having an inner portion manufactured from HDPE or similar material and an outer portion of Primacor or similar material.

It will be noted that catheter 100 may include any catheter type known in the art, for example a guiding catheter, an angioplasty catheter, a radiation delivery catheter, a stent deployment catheter, an imaging catheter, a drug delivery catheter, as well as any other type of medical catheters used in the field. Although catheter 100 is shown with an "over-the-wire" (OTW) catheter configuration, this invention is not limited to such catheter arrangements only. Those skilled in the art will recognize that this invention may also be practiced using a catheter with a "standard Rapid Exchange" (standard RX), "tip-RX", or any other catheter configuration known in the art. Furthermore, catheter 100 may have a single lumen inner member 104 (as shown in FIG. 3A), or alternatively, catheter 100 may have a multi-lumen inner member configuration (as shown in cross-sectional catheter views of FIGS. 3B–3C). In addition, to practice this invention, the catheter need not incorporate an inflatable balloon.

Continuing with reference to FIGS. 2 and 3A–3C, in an embodiment, optical fiber 30 is a single strand, single-mode glass optical fiber typically extending slightly beyond both the proximal and distal ends 128, 110 of catheter 100. A proximal extension length 34 of optical fiber 30 allows for connection of the optical fiber 30 to an LDV system 62 through a mechanical coupler 66 and an LDV optical fiber 68. A distal extension length of optical fiber 30 allows for any necessary steps required to make the optical fiber tip flush with, or extend slightly beyond the distal end 110 of catheter 100. Such steps can include, but are not limited to, cleaving the optical fiber 30 at an angle, cutting the fiber 30 with a perpendicular face, or removing the fiber cladding as necessary to optimize light transmission/reception.

The arrangement, sizes, material, etc. of the optical fiber 30 used with therapeutic catheter 100 have been described. Furthermore, as stated above, it is within the scope of the present invention to have the therapeutic catheter 100 incorporate multiple optical fibers or a fiber optic bundle for the optical fiber 30. This arrangement may be advantageous for applications that would require performing LDV measurements simultaneously at multiple sites in a vessel.

Guidewire for Performing LDV Blood Flow Measurements to Locate Coronary Sinus

Figure 4:
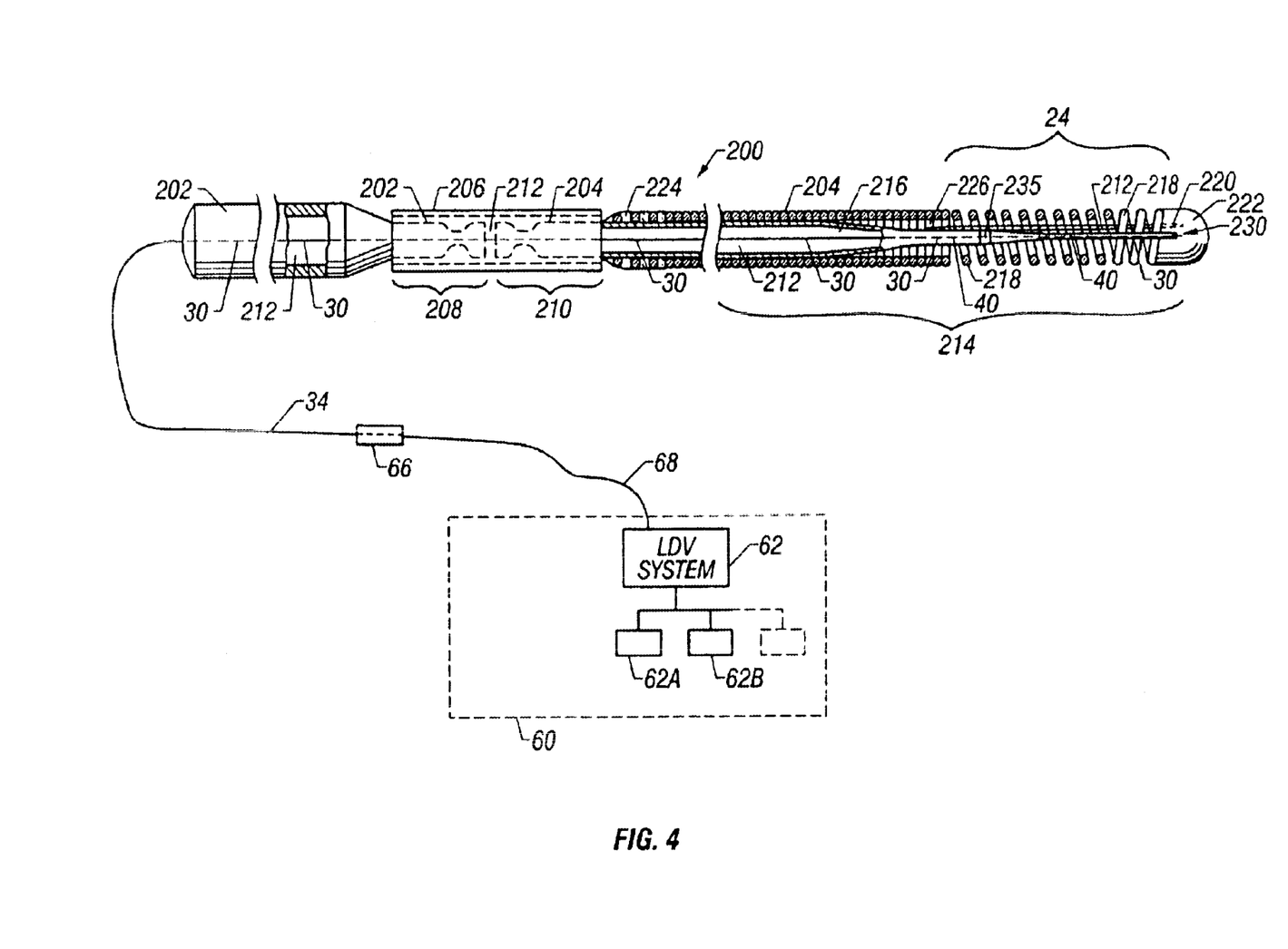
FIG. 4 illustrates generally an embodiment of a therapeutic guidewire for locating the coronary sinus of a patient's heart coupled to an LDV apparatus and data processing system.

FIG. 4 illustrates generally an embodiment of a guidewire 200 for performing laser Doppler velocimetry (LDV) measurements coupled to a data processing system 60. Guidewire 200 is adapted to be inserted into a patient's body lumen, such as an artery or vein and then advanced toward the heart area to locate a coronary. Any type and/or construction guidewire 200 used in the art may be employed within the scope of this invention. Depending on the type of application in which is to be used, the guidewire 200 is operatively coupled to a variety of intravascular/intraluminal treatment devices, including for example a balloon dilatation catheter for percutaneous transluminal coronary angioplasty (PTCA) and percutaneous transluminal angioplasty (PTA) procedures, an intravascular/intraluminal stent, a directional atherectomy device, a drug delivery device, a radiation treatment device, or any other intravascular/intraluminal treatment device used in the art.

Continuing with reference to FIG. 4, in one embodiment, the guidewire 200 includes an elongated core member that has a relatively high strength proximal core section 202 and a relatively short flexible distal core section 204. Depending on manufacturing preferences, type of application used, etc., guidewire 200 may include a connecting element 206 that joins a distal end 208 of the proximal core section 202 and a proximal end 210 of the distal core section 204. An optical fiber 30 extends longitudinally through at least a portion of a lumen 212 that may be common to the proximal core section 202, the connecting element 206 and the distal core section 204. Alternatively, optical fiber 30 may extend longitudinally along the outside of the proximal core section 202, the connecting element 206 and the distal core section 204. The optical fiber 30 is for performing a laser Doppler velocity measurement of a fluid, e.g. blood within the body lumen.

In one embodiment, proximal core section 202 and distal core section 204 are each formed from a hypotube made of stainless steel (SS) or of a pseudoelastic alloy material, such as Nickel-Titanium (Ni—Ti) alloy (e.g., Nitinol). The connecting element 206 is configured as a sleeve or hollow member that slightly overlaps the distal end 208 of proximal core section 202 and the proximal end 210 of distal core section 204. It should be noted that various configurations and/or shapes may be practiced within the scope of this invention.

Continuing with reference to FIG. 4, in the embodiment shown, the distal core section 204 has at least one tapered section 216 that becomes smaller in the distal direction. The tapered shape of distal core section 204 enhances the mechanical performance of the guidewire 200. Alternatively, the distal core section 204 may have a non-tapered shape, which generally simplifies the guidewire manufacturing process.

A flexible coil 218, generally having a helical configuration, is disposed about the distal core section 204. Flexible coil 218 may be secured at its distal end to the distal end of a shaping ribbon 220 by a mass of bonding material, such as solder, which forms rounded tip 222 when it solidifies. The proximal end of the helical coil 218 may be secured to the distal core section 204 at a proximal location 224 and at intermediate location 226 by a suitable bonding material, e.g. solder. The proximal end of the shaping ribbon 220 may be secured to the distal core section 204 at the same intermediate location 226 by the bonding material, e.g. solder. The most distal section 228 of the helical coil 218 may be made of radiopaque metal, such as platinum or platinum-nickel alloys, to facilitate the fluoroscopic observation thereof while it is disposed within a patient's body.

In an embodiment, optical fiber 30 is exposed to a blood vessel of a patient at the distal tip 230 of the guidewire 200.

Alternatively, guidewire 200 may have at least one opening 232, such as a window or a cutaway in its wall that allows optical fiber 30 to be exposed to a patient's vasculature and perform LDV measurements. Opening/window 232 may have any size and/or shape that is advantageous to optical fiber 30, guidewire 200 and/or guidewire manufacturing preferences. Alternatively, optical fiber 30 may be exposed to a patient's vasculature through guidewire coil 218.

With reference to FIG. 4, the most distal part 214 of the distal core section 204 may be manufactured to have various shapes and configurations, for example: tapered and plunge-ground to a specific length, plunge-ground to a specific length only, or flattened into a rectangular cross-section. It will be noted that guidewire embodiments other than the exemplary guidewire embodiment shown in FIG. 4 may be used to practice this invention. For example, a guidewire having a continuous tubular body (instead of having distal and proximal sections and a connecting element) may be employed with this invention.

The distal core section 204 can be made of a pseudoelastic alloy material, such as Nickel-Titanium (Ni—Ti) alloy (e.g., Nitinol). In one embodiment, the Ni—Ti alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. In an embodiment, distal core section 204 has a length in a range of approximately 5–20 centimeters and an outer diameter of about 0.006–0.018 inches.

The elongated proximal core section 202 of the guidewire 200 is generally about 130 to about 300 centimeters in length with an outer diameter of about 0.006 to 0.018 inches (0.15–0.45 millimeters) for coronary use. Larger diameter guidewires, e.g. up to 0.035 inches (0.89 millimeters) or more may be employed in peripheral arteries and other body lumens. The lengths of the smaller diameter and tapered sections can range from about 1 to about 20 centimeters, depending upon the stiffness or flexibility desired in the final product. The helical coil 218 may be about 3 to about 45 centimeters in length, preferably about 5 to about 20 centimeters, has an outer diameter about the same size as the outer diameter of the elongated proximal core section 202, and is made from wire about 0.001 to about 0.003 inches (0.025–0.08 millimeters) in diameter, typically about 0.002 inches (0.05 millimeters). The shaping ribbon 220 and the flattened distal portion of distal core section 204 generally have rectangular-shaped transverse cross-sections which usually have dimensions of about 0.0005 to about 0.006 inches (0.013–0.152 millimeters), preferably about 0.001 by 0.003 inches (0.025–0.076 millimeters).

The high strength proximal core section 202 of guidewire 200 generally is significantly stronger than the pseudoelastic distal portion. Suitable high strength materials include 304-stainless steel, which is a conventional material in guidewire construction. Other high strength materials include nickel-cobalt-molybdenum-chromium alloys such as commercially available MP35N alloy.

It will be noted that the above describes an exemplary guidewire configuration. Those skilled in the art will recognize that the therapeutic guidewire for performing LDV blood flow measurements of this invention may be practiced using other guidewire configurations and arrangements known in the art.

Continuing with reference to FIG. 4, in an embodiment, optical fiber 30 is a single strand, single-mode glass optical fiber typically extending slightly beyond both the proximal and distal ends of guidewire 200. A proximal extension length 34 of optical fiber 30 allows for connection of the optical fiber 30 to an LDV system 62 through a mechanical coupler 66 and an LDV optical fiber 68. A distal extension length of optical fiber 30 allows for any necessary steps required to make the optical fiber tip flush with, or extend slightly beyond the distal end 230 of guidewire 200. Such steps can include, but are not limited to, cleaving the optical fiber 30 at an angle, cutting the fiber 30 with a perpendicular face, or removing the fiber cladding as necessary to optimize light transmission/reception.

The arrangement, sizes, material, etc. of the optical fiber 30 used with guidewire 200 have been described. Furthermore, as stated above, it is within the scope of the present invention to have the guidewire 200 incorporate multiple optical fibers or a fiber optic bundle for the optical fiber 30. This arrangement may be advantageous for applications that would require performing LDV measurements simultaneously at multiple sites in a vessel.

During its use in a medical procedure, the optical fiber 30 of therapeutic guidewire 200 transmits and receives light for determining fluid flow velocities through a laser Doppler velocimetry (LDV) technique. As stated above, to perform LDV measurements, light is transmitted from a laser source 62A in the LDV system 62 through the optical fibers 30, 34, 68 and is scattered off of formed blood elements. The scattered light is collected by a detector 62B in the LDV system 62 as the light travels back through the optical fibers 30, 34, 68. The frequency content of the scattered light is indicative of the fluid velocity at the measurement site.

Method for Performing LDV Blood Flow Measurements to Locate the Coronary Sinus FIGS. 1, 2 and 4 illustrate exemplary embodiments of an intravascular device 10 for performing laser Doppler velocimetry blood flow measurements coupled to a LDV apparatus and processing system 60. The intravascular device 10 may include any medical device, such as a catheter or a guidewire, used to treat intravascular conditions.

With reference to FIGS. 1, 2 and 4, in an embodiment of a medical procedure, a distal portion of intravascular device 10 (or catheter 100, guidewire 200) is inserted into a patient according to commonly known methods. Depending upon the type of medical procedure being performed, other medical devices may be coupled to device 10 (or catheter 100, guidewire 200). For example, if catheter 200 is to be used in a stenting procedure, an expandable metallic structure, such as stent (not shown), may be disposed, i.e., loaded, over the distal most tip of catheter body, typically over the balloon 108.

Hub or coupler 66 couples optical fiber 30 (and its extension length 34) to an LDV system 62 via connecting optical fiber 68. The LDV system 62 may include various equipment known in the art of laser Doppler velocimetry measurement, for example a laser source 62A, a detector 62B, etc. Detector 62B may further include an amplifier (not shown), a signal processing unit (not shown), a computer system (not shown) which are to process the feedback signal received through the fiber optics 30, 34, 66. It is appreciated that any or all of laser source, amplifier, signal processing unit, computer system, etc. can be combined into an independent console unit.

Laser source 62A can be any continuous-wave signal or a high-repetition-rate pulsed laser. In one embodiment, laser source 62A is a modulated light diode or high-powered laser light source. The laser source is typically chosen based on the light wavelengths and light source power that facilitate the detection of the particular physical characteristic or variable. Specifically, because the light transmission window of blood is in the red to infrared (IR) range, a light wavelength in the range of 700 nm to 1500 nm may be used. It should be noted that longer wavelengths in the above stated range are desirable as they overcome some of the signal loss due to scattering in the blood. The shorter wavelengths are more energetic and therefore have the potential to cause tissue damage. In one embodiment, a wavelength of approximately 1300 nm may preferably be used.

The light output could be filtered if desired, as a homogenized illumination improves the signal-to-noise ratio. If the red or near-IR spectral range is used, laser diodes could be used as the excitation source to further improve the signal-to-noise ratio. Signal processing unit typically processes a signal from visual or light source data to electronic data or vice versa.

It is appreciated that a variety of components can be used to help generate, transmit and receive fiber optic signals. For example, a mono-chromator can be used to receive light signals transmitted back from the field of interest. The mono-chromator can also be fitted with a photodiode array detector, such as a 512 element intensified silicon photodiode array detector. Furthermore, a high-resolution filter grating can be installed in the mono-chromator in order to sharpen the features displayed in the spectral response for easier peak recognition and spectral analysis. A pulse generator can be used to time the detector response from the output pulse of the laser light signal.

In a typical embodiment of the present invention, a physician, e.g. cardiologist, usually first decides what portion of a vessel/treatment site is to be investigated, e.g., LDV flow measured. The physician will generally then insert the intravascular device 10, 100, 200 with optical fiber 30 into the patient's vasculature and advance it to a specified location in the vasculature. Inserting and advancing medical device 10, 100, 200 is performed using methods well known in the art. Once the medical device 10, 100, 200 is in place, the LDV apparatus and processing system 60 is operated to send and receive a plurality of light signals. The received reflected light signals are processed by the data processing system to provide information on a display such that the doctor can view this information and determine how to proceed.

Generally, to perform LDV blood flow measurements, light is transmitted from laser source 62A in the LDV system 62 through the optical fibers 30, 34, 68 and is scattered off of formed blood elements 52. The scattered light is collected by detector 62B in the LDV system 62 as the light travels back through the optical fibers 30, 34, 68. The frequency content of the scattered light is indicative of the fluid velocity at the measurement site.

In an alternative embodiment, the LDV apparatus 60 uses two or more intersecting beams from a light source 62A, for example a laser source, and advanced optical data collection and processing equipment 62B to measure motion of individual minute particles as they pass through an imposed fringe pattern. The crossing of laser beams creates a "measurement volume" which consists of an interference fringe pattern of planar layers of high and low intensity light. Minute particles (e.g., 1 $\mu$m to 10 $\mu$m) present in the fluid backscatter the laser light with a frequency proportional to the flow velocity when passing through the measurement volume. The backscattered light is typically converted to an electrical signal with a photodetector or similar device. By using Fast Fourier Transform (FFT) techniques, the Doppler frequency is determined. The flow velocity is calculated with the known distance between the interference fringes and the measured frequency.

To locate the coronary sinus, the physician performs a plurality of LDV measurements within a predetermined (i.e., preselected) area of the patient's heart. While maneuvering the intravascular device within the area, the physician determines the coronary sinus of the heart by determining the laser Doppler velocity measurement having the maximum value from the plurality of laser Doppler velocity measurements conducted.

EXPERIMENTAL RESULTS

Catheter and guidewire based systems employing the features of this invention have been evaluated. LDV blood flow evaluation tests were conducted in anti-coagulated sheep blood in a benchtop pulsatile flow.

Figure 5:
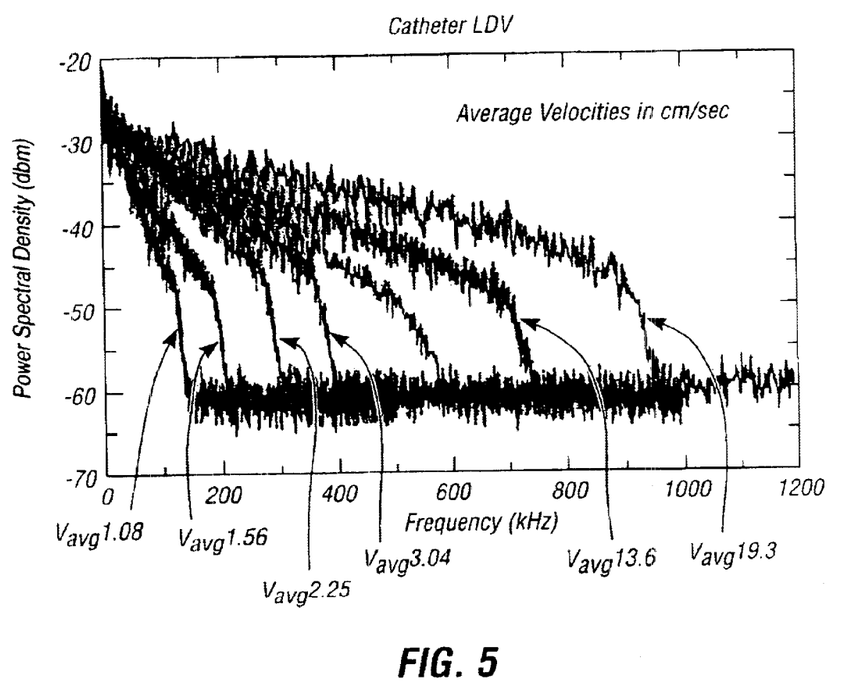
FIG. 5 shows Fast Fourier Transform (FFT) spectra obtained at peak output, averaged over multiple successive cycles, for a range of pump speeds conducted with a tested catheter prototype/LDV system.

FIG. 5 shows data obtained with a tested catheter prototype/LDV system that employed a 155 microns (micrometers, $\mu$m) glass fiber optic (having a 9.3 $\mu$m core) for the catheter prototype and a 250 $\mu$m glass (with a 9.3 $\mu$m core) LDV fiber optic. FIG. 5 shows Fast Fourier Transform (FFT) spectra obtained at peak output using the catheter system for a range of pump speeds (identified on the plots as $V_{avg}$) from 1.08–19.3 cm/s. The known pump flow speed is equivalent to the average flow velocity over the cross-sectional area of the tubing. The units on the axes are signal intensity (negative millidecibels, dB) versus frequency (kHz). The key feature of the spectra is the drop-off frequency at each flow speed, which corresponds to the most vertical region of each individual trace. For each peak output trace, the drop-off frequency corresponds to the average fluid flow velocity (as determined by the LDV system) at the measurement site. FIG. 5 demonstrates the sensitivity of the LDV/catheter system 100 to recording peak output flow signals over a range of pump speeds, and therefore over a range of fluid velocities.

Figure 6:
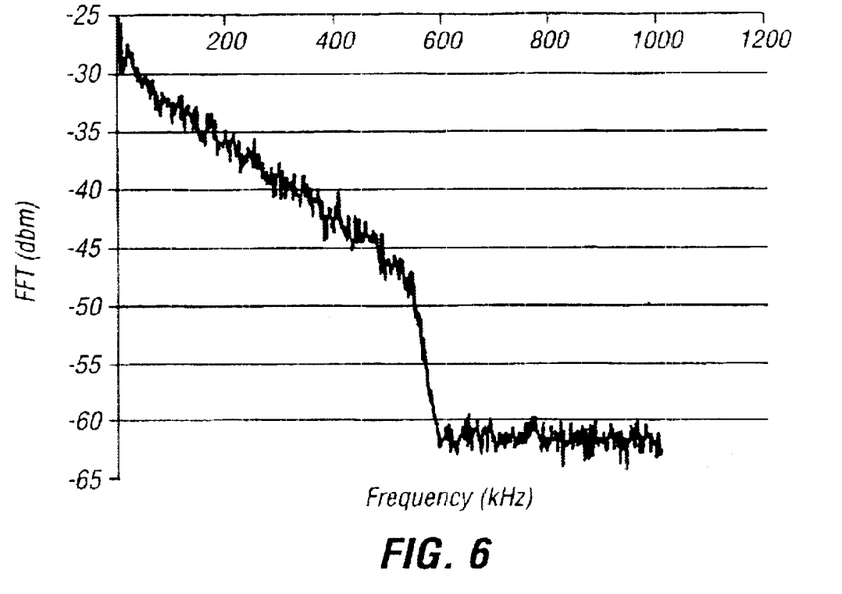
FIG. 6 shows FFT spectra obtained at peak output conducted with a tested guidewire prototype/LDV system.
Figure 7:
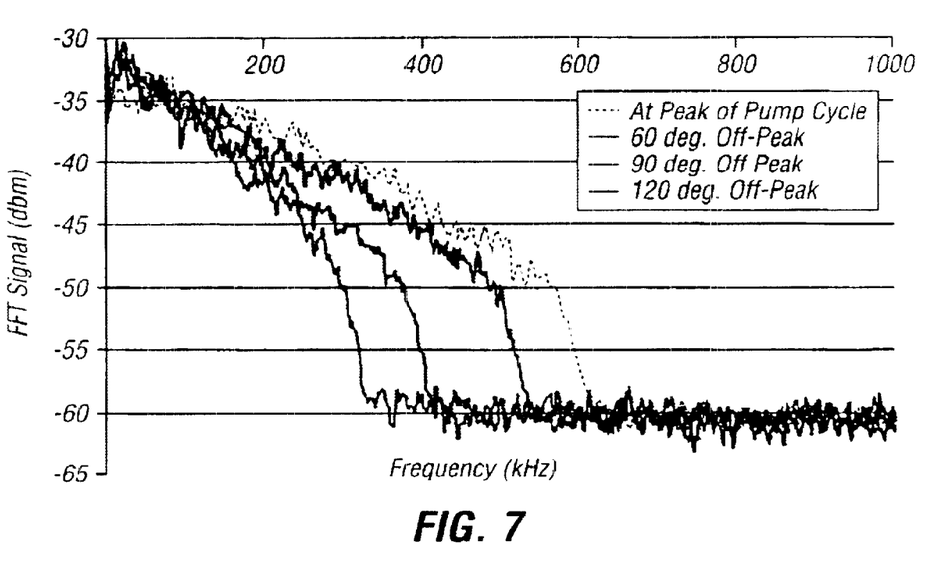
FIG. 7 shows FFT spectra at various pump cycle phases conducted with a tested guidewire prototype/LDV system.
Figures 8A, 8B, 8C, 8D, 8E:
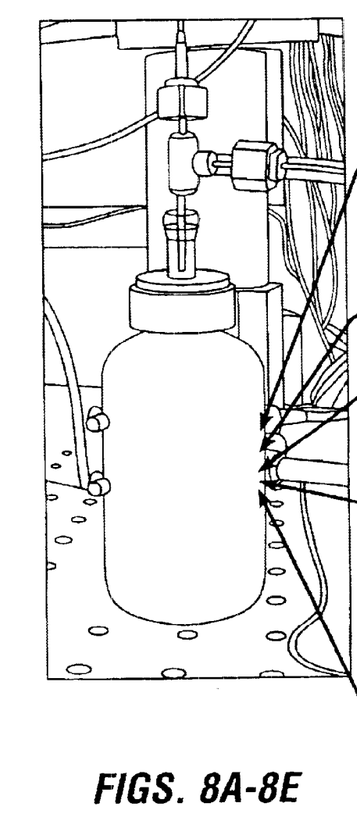
FIGS. 8A–8E show SPD spectra at five different measurement points conducted on a simulated coronary sinus model using a prototype fiber optic device/LDV system.
Figure 8A:
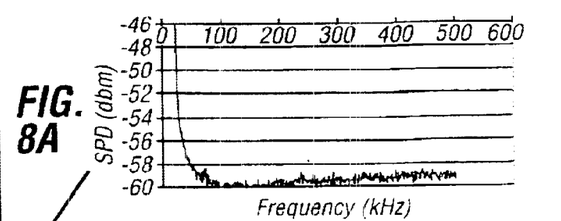
Figure 8B:
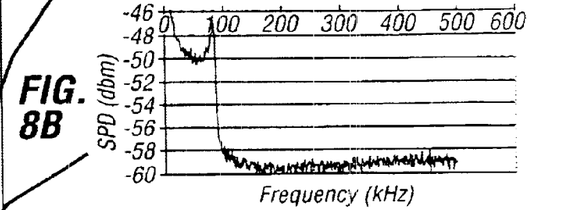
Figure 8C:
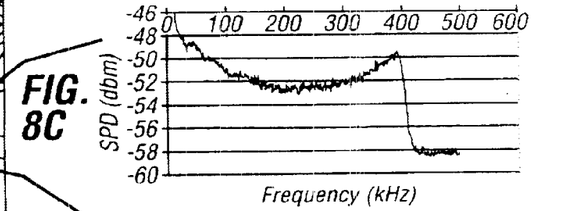
Figure 8D:
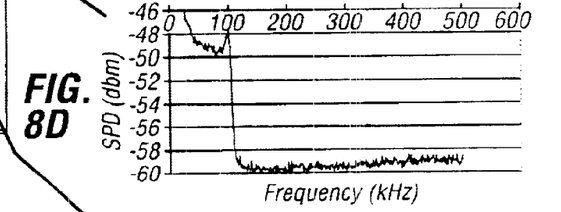
Figure 8E:
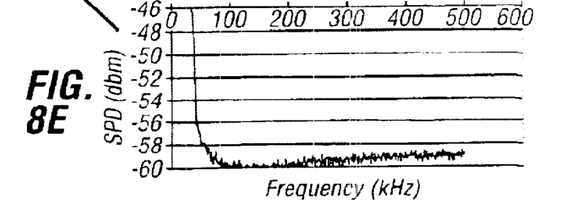

FIGS. 6–7 relate to data obtained with a tested guidewire prototype/LDV system that employed a 155 microns (micrometers, $\mu$m) glass fiber optic (having a 9.3 $\mu$m core) for the catheter prototype and a 250 $\mu$m glass (with a 9.3 $\mu$m core) LDV fiber optic. FIG. 6 shows a Fast Fourier Transform (FFT) spectrum obtained at peak output, averaged over multiple successive cycles for the guidewire system. The units on the axes are intensity (negative mdB) versus frequency (kHz). This spectrum was obtained under peak output conditions, when the average velocity over the pump cycle was 18 cm/s. The key feature of the spectrum is the drop-off frequency, which corresponds to the steep region of the plot at approximately 560 kHz. At a given instant in the pump cycle, the drop-off frequency corresponded to the flow velocity. To determine particle velocity using the LDV technique, the raw Doppler signal is digitized and from the digitized signal FFT cross-spectra and power spectra are constructed, giving the Doppler frequency. The magnitude of the particle velocity is proportional to the Doppler frequency divided by the fringe spacing. FIG. 6 demonstrates the sensitivity of the LDV/guidewire system to recording peak output flow signals.

FIG. 7 shows FFT spectra obtained at various phases of pump cycle, the result of averaging over multiple successive cycles. The signal phases are as indicated in the legend (the signal labeled "at peak of pump cycle" is identical to that in FIG. 6). FIG. 7 demonstrates the temporal/phase sensitivity of the LDV/guidewire system throughout the pump cycle.

FIGS. 8A–8E show the SPD spectra at five different measurement points conducted on a simulated coronary sinus model using a prototype fiber optic device/LDV system. As the LDV system is positioned (i.e., maneuvered) over the general area having the simulated coronary sinus model, the LDV signal changes (i.e., velocity changes) indicate whether the device is at the edges of the simulated coronary sinus (see graphs on FIGS. 8A and 8E) or near the center of the coronary sinus (see FIG. 8C) which is indicated by the point having the signal with the maximum frequency (and thus the maximum flow velocity).

Thus, the present invention describes an apparatus and method for locating the coronary sinus of a patient's heart through the use of a intravascular device having laser Doppler velocimetry (LDV) blood flow measurement capabilities. The LDV technique is known for high accuracy (up to 0.1%), a wide measuring range and for its high spatial and time resolution. The technique has been shown to have great potential for conducting in vivo blood flow measurements, even in challenging arterial anatomies. By integrating LDV technology into a therapeutic guidewire system or a therapeutic catheter system, medical professionals would be able to quickly identify the coronary sinus of a patient's heart, a situation that will inevitably lead to improvements in both acute and chronic clinical outcomes for heart procedures.

We claim:

1. A system for locating a coronary sinus of a patient's heart, the system comprising:
    a laser Doppler velocimetry system; and
    a catheter comprising an elongated shaft having an inner tubular member with a lumen extending therethrough, an the outer member disposed about the inner tubular member, and an intraluminal gap formed between the outer and inner members, the catheter further comprising at least one optical fiber extending through the intraluminal gap, the optical fiber having a distal end configured to contact with a blood flow within the patient's heart and a proximal end coupled to the laser Doppler velocimetry system to perform a plurality of laser Doppler velocity measurements of the blood flow within the heart to locate the coronary sinus of the heart.

2. A method for locating a coronary sinus of a patient's heart, the method comprising:
    inserting an intravascular device into a vasculature of a patient, the intravascular device comprising an elongated member having distal and proximal sections and at least one lumen extending therethrough, the intravascular device further comprising at least one optical fiber extending through the lumen, the optical fiber having a distal end configured to contact with a blood flow within the patient's heart and a proximal end coupled to a laser Doppler velocimetry system;
    advancing the intravascular device to a predetermined startup location within the right atrium of patient's heart;
    performing a plurality of laser Doppler velocity measurements of the blood flow within the heart while moving the intravascular device from the predetermined startup location over a plurality of locations within the right atrium of patient's heart; and
    determining the laser Doppler velocity measurement having the maximum value from the plurality of laser Doppler velocity measurements.

3. The method of claim 2 wherein the intravascular device is a catheter.

4. The method of claim 2 wherein the intravascular device is a guidewire.

5. A guidewire for locating a coronary sinus of a patient's heart, the guidewire comprising:
    an elongated guidewire body having a lumen extending therethrough;
    an atraumatic distal tip formed at a distal end of the distal core section; and
    at least one optical fiber longitudinally disposed through the lumen, the optical fiber having a distal end to contact with a blood flow within the patient's heart and a proximal end to couple to a laser Doppler velocimetry system for performing a plurality of laser Doppler velocity measurements of the blood flow within the heart to locate the coronary sinus of the heart.

6. The guidewire of claim 5 wherein the guidewire body comprises a distal core section, a proximal core section, and a connecting member coupling a proximal end of the distal core section to a distal end of the proximal core section.

7. The guidewire of claim 5 further comprises a flexible coil disposed about the distal core section of the elongated guidewire body, the flexible coil coupled to at least one point along the distal core section.

8. The guidewire of claim 5 further comprises a shaping ribbon coupled to the distal core section.

9. The guidewire of claim 5 wherein the guidewire is operatively coupled to an intravascular device for providing treatment to the patient's heart before, during or after locating the coronary sinus.

10. A catheter for locating a coronary sinus of a patient's heart, the catheter comprising:
    an elongated shaft having an inner tubular member with a lumen extending through at least a portion thereof, an outer member disposed about the inner tubular member, and an intraluminal gap formed between the outer and inner members; and
    at least one optical fiber extending through the intraluminal gap, the optical fiber having a distal end to contact with a blood flow within the patient's heart and a proximal end to couple to a laser Doppler velocimetry system to perform a plurality of laser Doppler velocity measurements of the blood flow within the heart to locate the coronary sinus of the heart.

11. The catheter of claim 10 further comprises an atraumatic tip coupled to a distal end of the inner tubular member.

12. The catheter of claim 10 wherein the lumen is configured to receive a guidewire therethrough for positioning the catheter within a desired treatment site within the patient's heart.

13. The catheter of claim 10 wherein the lumen is configured to receive a therapeutic drug therethrough.

14. The catheter of claim 10 wherein the outer member is a braided member.

15. The catheter of claim 14 wherein the braided member is configured to transmit a 1:1 torque ratio to a distal tip of the catheter when a steering force is applied from an adapter coupled to a proximal end of the elongated shaft.

16. The catheter of claim 10 further comprises an expandable member coupled to a distal portion of the elongated shaft.

17. The catheter of claim 16 wherein the lumen is configured to receive an inflation medium therethrough for expanding the expandable member.

18. The catheter of claim 16 wherein the expandable member is a balloon.

19. An intravascular device for locating a coronary sinus of a patient's heart, the intravascular device comprising:
   an elongated member having at least one lumen; and
   at least one optical fiber coupled to the elongated member, the optical fiber having a distal end to contact with a blood flow within the patient's heart and a proximal end to couple to a laser Doppler velocimetry system to perform a plurality of laser Doppler velocity measurements of the blood flow within the heart to locate the coronary sinus of the heart.

20. The intravascular device of claim 1 further comprises an atraumatic tip connected to a distal end of the elongated member.

21. The intravascular device of claim 1 wherein the optical fiber is positioned through the lumen and is coupled to an inner surface of the elongated member.

22. The intravascular device of claim 1 wherein the optical fiber is movable within the lumen of the elongated member.

23. The intravascular device of claim 1 wherein the elongated member has a second lumen longitudinally disposed therethrough.

24. The intravascular device of claim 23 wherein the second lumen is configured to slidably receive a guidewire therethrough for positioning the intravascular device within a desired site within the patient's heart.

25. The intravascular device of claim 23 wherein the second lumen is configured to receive a therapeutic drug therethrough.

26. The intravascular device of claim 23 further comprises an expandable member coupled to the distal section of the elongated member.

27. The intravascular device of claim 26 wherein the second lumen is configured to receive an inflating medium therethrough for expanding the expandable member.

* * * * *

UNITED STATES PATENT AND TRADEMARK OFFICE
CERTIFICATE OF CORRECTION

PATENT NO. : 6,697,667 B1
DATED : February 24, 2004
INVENTOR(S) : Lee et al.

It is certified that error appears in the above-identified patent and that said Letters Patent is hereby corrected as shown below:

Title page,
Item [56], References Cited, OTHER PUBLICATIONS,
"Kilpatrick D" reference, please delete "Lase" and insert -- Laser --.
"Stefandadis C" reference, please delete "Coronay" and insert -- Coronary --.
"Deborah Kilpatrick" reference, please delete "Mountain View" and insert -- Los Altos --.
"Bridget A. Hurley" reference, please delete "Mountain View" and insert
-- San Francisco --.
"Jeffrey T. Ellis" reference, please delete "Mountain View" and insert -- San Francisco --.

Signed and Sealed this

Fifth Day of October, 2004

JON W. DUDAS
*Director of the United States Patent and Trademark Office*